US00PP15694P2

(12) United States Plant Patent
Slaughter et al.

(10) Patent No.: US PP15,694 P2
(45) Date of Patent: Mar. 22, 2005

(54) NECTARINE TREE 'BURNECTSEVENTEEN'

(50) Latin Name: *Prunus nucipersica*
Varietal Denomination: Burnectseventeen

(75) Inventors: John K. Slaughter, Clovis, CA (US); Timothy J. Gerdts, Kingsburg, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 0 days.

(21) Appl. No.: 10/746,444

(22) Filed: Dec. 23, 2003

(51) Int. Cl.[7] ..... A01H 5/00
(52) U.S. Cl. ..... Plt./190
(58) Field of Search ..... Plt./190

*Primary Examiner*—Bruce R. Campell
*Assistant Examiner*—S. B. McCormick-Ewoldt
(74) *Attorney, Agent, or Firm*—Wells St. John P.S.

(57) ABSTRACT

A new and distinct variety of nectarine tree (*Prunus nucipersica*), and which is denominated varietally as 'Burnectseventeen', and which produces an attractively colored yellow-fleshed, clingstone nectarine which is mature for harvesting approximately August 7th to August 12 under ecological conditions prevailing in the San Joaquin Valley of central California.

1 Drawing Sheet

BACKGROUND OF THE NEW VARIETY

The present invention relates to a new, novel and distinct variety of nectarine tree, '*Prunus nucipersica*', which has been denominated varietally as 'Burnectseventeen' hereinafter.

The present variety of nectarine tree resulted from an on-going program of fruit and nut tree breeding. The purpose of this program is to improve the commercial quality of deciduous fruit and nut varieties, and rootstocks, by creating and releasing promising selections of *prunus, malus* and *regia* species. To this end we make both controlled and hybrid cross pollinations each year in order to produce seedling populations from which improved progenies are evaluated and selected.

The seedling 'Burnectseventeen' was originated by us from a population of seedlings grown in our experimental orchards located near Fowler, Calif. The seedlings, grown on their own roots, were the result of a controlled cross of an un-named yellow-fleshed clingstone nectarine tree (nonpatented), which was used as the pollen parent, and A40.002, an un-named, late ripening, yellow-fleshed, clingstone peach tree, of known parentage (unpatented), which was used as the seed parent. One seedling, which is the present variety, exhibited especially desirable characteristics and was marked for subsequent observation. After the 1999 fruiting season, the new variety of nectarine tree was selected for advanced evaluation and repropagation.

ASEXUAL REPRODUCTION

Asexual reproduction of this new and distinct variety of nectarine tree was accomplished by budding the new peach tree to 'Nemaguard' Rootstock (non-patented). This was performed by us in our experimental orchard located near Fowler, Calif. Subsequent evaluations have shown those asexual reproductions run true to the original tree. All characteristics of the original tree, and its fruit, were established and appear to be transmitted through succeeding asexual propagations.

SUMMARY OF THE VARIETY

'Burnectseventeen' is a new and distinct variety of nectarine tree, which is considered of large size, and which has vigorous growth. This new nectarine tree is also a regular and productive bearer of relatively large, firm, yellow fleshed, clingstone fruit which have good flavor and eating qualities. This new tree has a medium chilling requirement of approximately 650 hours, and further produces relatively uniformly sized fruit throughout the tree. The fruit produced by this new variety has a non-melting flesh which makes it ideal for storage. In addition, the fruit also appears to have good handling and shipping qualities. Still further, the 'Burnectseventeen' nectarine tree bears fruit which are ripe for commercial harvesting and shipment on approximately August 7 to August 12 under the ecological conditions prevailing in the San Joaquin Valley of central California. In relative comparison to the seed parent of the new variety, the present nectarine tree bears fruit about 14 or more days earlier at the same geographical location. In relative comparison to other known varieties, the present variety of nectarine tree is most closely similar to the "Summer Blush" Nectarine (U.S. Plant Pat. No. 8,002) which, when grown in a natural state, produces fruit having about 45% to about 60% blush over the fruit surface. In contrast to this characteristic, the present variety produces fruit which has a deep red blush which covers about 80% to about 90% of the fruit surface.

BRIEF DESCRIPTION OF THE DRAWING

The accompanying drawing, is a color photograph of the present variety. This photograph depicts two whole mature fruit, and one fruit dissected substantially in the equatorial plane, and which reveals the flesh and the stone characteristics thereof. The external coloration of the fruit, as shown, is sufficiently matured for harvesting and shipment. Additionally, the photograph displays a typical stone, with the flesh removed. The colors in this photograph are as nearly true as is reasonably possible in a color representation of this type. Due to chemical development, processing and printing, the leaves and fruit depicted in these photographs may or may not be accurate when compared to the actual specimen. For this reason, future color references should be made to the color plates (Royal Horticultural Society) and other more general color descriptions provided hereinafter.

DETAILED DESCRIPTION

Referring more specifically to the pomological details of this new and distinct variety of nectarine tree, the following has been observed during the fifth fruiting season under the ecological conditions prevailing at orchards which are located near the town of Fowler, county of Fresno, state of California. All major color code designations are by reference to The R.H.S. Colour Chart (Fourth Edition) and which is provided by The Royal Horticultural Society of Great Britain. Common color names are also occasionally used.

TREE

Size:

*Generally.*—Considered medium as compared to other common commercial nectarine cultivars ripening in the late season of maturity. The tree of the present variety was pruned to a height of approximately 305.0 cm to about 325.0 cm at maturity.

Vigor: Considered moderately vigorous. The present nectarine tree variety grew from about 120.0 cm to about 130.0 cm in height during the first growing season. The new variety was pruned to a height of approximately 118.0 cm during the first dormant season, and primary scaffolds were then selected for the desired tree structure.

Productivity: Productive. Fruit set varies from about 1.5 to several times more than the desired crop load. Fruit set is spaced by thinning to develop the remaining fruit into the desired market sized fruit. The number of the fruit set varies with the prevailing climatic conditions, and cultural practices employed during the bloom period, and is therefore not distinctive of the present variety.

Bearer: Regular. Fruit set has been heavy during the years of observation and thinning was necessary during the past 5 years.

Form: Upright, and pruned to a vase shape.

Density: Considered medium dense. It has been discovered that pruning the branches from the center of the tree to obtain a resulting vase shape allows for air movement and appropriate amounts of sunlight to enhance fruit color and renewal of fruiting wood throughout the tree.

Hardiness: The present tree was grown and evaluated in USDA Hardiness Zone 9. Winter chilling requirements of the new tree are approximately 650 hours below 7.0 degrees C. The variety appears to be hardy under typical central San Joaquin Valley climatic conditions.

TRUNK

Diameter: Approximately 11.2 cm in diameter when measured at a distance of approximately 15.24 cm above the soil level. The measurement was taken at the end of the fifth growing season.

Bark texture: Considered moderately rough, with numerous folds of papery scarfskin being present.

Lenticels: Numerous flat, oval lenticels are present. The lenticels range in size from approximately 4.0 to about 7.0 millimeters in width, and from 1.0 to about 2.0 millimeters in height.

Lenticel color: Considered an orange brown, (RHS Greyed-Orange Group 168 B).

Bark coloration: Variable, but it is generally considered to be a medium grey-brown, (RHS Greyed-Orange Group 174 A).

BRANCHES

Size: Considered medium for the variety.

Diameter: Average as compared to other nectarine varieties. The branches have a diameter of about 4.8 centimeters when measured during the fourth year after grafting.

Surface texture: Average, and appearing furrowed on wood which is several years old.

Crotch angles: Primary branches are considered variable, and are between about 48 to 54 degrees when measured from the horizontal axis. This particular characteristic is not considered distinctive of the variety, however.

Current season shoots:

*Surface texture.*—Substantially glabrous.

Internode length: Approximately 2.2 to about 2.4 cm.

Color of mature branches: Medium brown, (RHS Greyed-Orange 177 D).

Current seasons shoots:

*Color.*—Light green, (RHS Green Group 137 D). The color of new shoot tips is considered a bright and shiny green (RHS Green Group 141D).

LEAVES

Size: Considered medium to large for the species. Leaf measurements have been taken from vigorous, upright, current-season growth at approximately mid-shoot.

Leaf length: Approximately 138.0 to about 165.0 millimeters.

Leaf width: Approximately 35.0 to about 40.0 millimeters.

Leaf base shape: Slightly oblique relative to the leaf longitudinal axis.

Leaf form: Lancelolate. Considered to be relatively narrow for the species.

Leaf tip form: Acuminate.

Leaf color:

*Upper leaf surface.*—Dark green, (approximately RHS Green Group 137 A).

Leaf texture: Glabrous.

Leaf color:

*Lower surface.*—Medium green, (RHS Yellow-Green Group 137 D).

Leaf venation: Pinnately veined.

Mid-vein:

*Color.*—Light yellow green, (RHS Yellow-Green Group 145 D).

Leaf margins: Slightly undulating.

Form: Considered crenate.

Uniformity: Considered generally uniform.

Leaf petioles:

*Size.*—Considered medium.

*Length.*—About 8.0 to about 10.0 mm.

*Diameter.*—About 1.5 to about 2.0 mm.

*Color.*—Pale green, (RHS Yellow-Green Group 145 D).

Leaf glands:

*Size.*—Considered medium. Approximately 1.5 mm in length, and about 1.0 mm in height.

*Number.*—Generally one gland per margin side. Occasionally two glands per margin side.

*Type.*—Reniform.

*Color.*—Considered a pale orange (RHS Orange-Red Group 30 C).

Leaf stipules:
*Size.*—Medium large for the variety.
*Number.*—Typically 2 per leaf bud and up to 6 per shoot tip.
*Form.*—Lanceolate in form and having a serrated margin.
*Color.*—Green, (RHS Yellow-Green Group 144 B) when young, but graduating to a brown color, (RHS Grey-Orange group 166 B) with advancing senescence. The stipules are considered to be early deciduous.

FLOWERS

Flower buds:
*Generally.*—The floral buds, depending upon the stage of development, are approximately 7.0 millimeters wide; about 11.0 millimeters long; conic in form; and slightly appressed relative to the bearing shoot.
Flower buds:
*Color.*—This characteristic is dependent upon the proximity to bloom. The bud scales are deep purple, (approximately RHS Greyed-Purple Group N186 B). The buds are considered hardy under typical central San Joaquin Valley climatic conditions.
Hardiness: No winter injury has been noted during the last several years of evaluation in the central San Joaquin Valley. The current variety has not been intentionally subjected to drought or heat stress, and therefore this information is not available.
Date of first bloom: Feb. 27, 2003.
Blooming time: Considered mid-season in relative comparison to other commercial nectarine cultivars grown in the central San Joaquin Valley. The date of full bloom was observed on Mar. 6, 2003. The date of bloom varies slightly with climatic conditions and cultural practices.
Duration of bloom: Approximately 9 days. This characteristic varies slightly with the prevailing climatic conditions.
Flower type: The variety is considered to have a showy type flower.
Flower size: Flower diameter at full bloom is approximately 34.0 to about 38.0 millimeters.
Bloom quantity: Considered abundant.
Flower bud frequency: Normally 1 to 2 flower buds appear per node.
Petal size:
*Generally.*—Considered medium for the species.
Length: Approximately 19.0 to about 21.0 millimeters.
Width: Approximately 16.0 to about 18.0 millimeters.
Petal form: Slightly ovoid.
Petal count: Nearly always 5.
Petal texture: Glabrous.
Petal color: Light pink, (RHS Red-Purple Group 62 C to a medium pink, (RHS Red-Purple Group 58 D).
Fragrance: Slight.
Petal claw:
*Form.*—The claw is considered generally ovoid and has a medium size when compared to other varieties.
*Length.*—Approximately 9.0 to about 11.0 millimeters.
*Width.*—Approximately 6.0 to about 8.0 millimeters.
Petal margins: Generally considered variable, from nearly smooth to slightly ruffled, to moderately undulate.
Petal apex:
*Generally.*—The petal apices are generally entire at the tip.

Flower pedicel:
*Length.*—Considered medium-long, and having an average length of approximately 5.0 to about 7.0 millimeters.
*Diameter.*—Considered average, approximately 2.0 millimeters.
*Color.*—A medium brown, (RHS Greyed-Orange Group 166 B).
Floral nectaries:
*Color.*—A dull orange, (RHS Greyed-Orange Group 167 A).
Calyx:
*Surface texture.*—Generally glabrous.
*Color.*—Purple, (approximately RHS Greyed-Red Group 181 B).
Sepals:
*Surface texture.*—The surface has a short, fine pubescent texture.
*Size.*—Average, and ovate in form.
*Color.*—A deep purple, (approximately RHS Greyed-Purple Group 187 A).
Anthers:
*Generally.*—Average in length.
*Color.*—Red to reddish-orange dorsally, (approximately RHS Greyed-Red Group 180 B).
Pollen production: Pollen is abundant, and has a yellow color, (approximately RHS Yellow-Orange Group 17 C). The present variety is considered self fruitful (self-pollinating).
Filaments:
*Size.*—Length is variable, approximately 12.0 to about 15.0 millimeters long.
Color: Considered light pink, (RHS Red-Purple Group 65 B).
Pistil:
*Number.*—Usually 1, rarely 2.
*Generally.*—Average in size.
*Length.*—Approximately 17.0 to about 19.0 millimeters including the ovary.
*Color.*—Considered a very pale green, (approximately RHS Yellow-Green Group 145 C).
*Surface texture.*—The variety has a long glabrous pistil.

FRUIT

Maturity when described: Firm ripe condition (shipping ripe).
Date of first picking: Aug. 7th, 2003. Date of last picking — Aug. 12, 2003. The date of harvest varies slightly with the prevailing climatic conditions.
Size:
*Generally.*—Considered large, and uniform.
Average cheek diameter: Approximately 72.0 to about 80.0 millimeters.
Average axial diameter: Approximately 68.0 to about 74.0 millimeters.
Typical weight: Approximately 277.0 grams. This characteristic is high dependent upon the prevailing cultural practices, and therefore is not particularly distinctive of the variety.
Fruit form:
*Generally.*—Considerably oblate. The fruit is generally uniform in symmetry.
Fruit suture: Very shallow and smooth, extending from the base to the apex. No apparent callousing or stitching exists along the suture line.

Suture:
*Color.*—This has a yellow background color, (approximately RHS Yellow-Orange Group 20 B).
Ventral surface:
*Form.*—Only slightly indented.
Apex: Rounded.
Base: Generally retuse.
Stem cavity: Generally elongated in the suture plane. Average depth of the stem cavity is about 8.0 mm. Average width of the stem cavity is about 12 mm.
Fruit skin:
*Thickness.*—Considered medium in thickness, and tenacious to the flesh.
*Texture.*—Glabrous.
*Taste.*—Non-astringent.
*Tendency to crack.*—None observed.
Color:
*Blush color.*—This blush color is generally red (approximately RHS Orange-Red Group N34 A). The blush covers approximately 80–90% of the fruit skin surface. The percentage of the blush on the fruit skin surface can vary, and is generally dependant upon the prevailing conditions under which the fruit was grown.
*Ground color.*—Yellow orange, (approximately RHS Yellow-Orange Group 21 C).
Fruit stem: Medium in length, approximately 5.0 to about 7.0 millimeters.
Diameter: Approximately 2.0 to about 3.0 millimeters.
Color: Pale yellow-green, (approximately RHS Yellow-Green Group 144 B).
Flesh:
*Ripens.*—Evenly.
*Texture.*—Firm, juicy and dense. The flesh is considered non-melting.
*Fibers.*—Few, small, and tender ones are typically found.
*Aroma.*—Very slight.
*Eating quality.*—Considered very good.
*Flavor.*—Considered sweet and mildly acidic. The flavor is considered both pleasant and balanced.
*Juice.*—Moderate.
*Brix.*—About 14.0 degrees. This characteristic varies slightly with the number of fruit per tree; prevailing cultural practices; and the surrounding climatic conditions.
*Flesh color.*—Pale yellow-orange, (approximately RHS Yellow-Orange Group 17 C).

STONE

Type: Clingstone.
Size: Considered medium for the variety. The stone size varies significantly depending upon the tree vigor, crop load and prevailing growing conditions.
Length: Average, about 28.0 to about 33.0 millimeters.
Width: Average, about 24.0 to about 27.0 millimeters.
Diameter: Average, about 16.0 to about 18.0 millimeters.
Form: Ovoid.
Base: The stone is usually rounded to slightly oblique relative to the ventral side.
Apex:
*Shape.*—The stone apex has a small prominent tip.
Stone surface:
*Surface texture.*—The pit is irregularly furrowed toward the apical end. Pitting is generally more present and noted on the lateral sides and toward the base.
*Ridges.*—The surface texture is generally characterized by more prominent ridges along the ventral edges and is more prominent at the apical tip.
Ventral edge:
*Width.*—Considered medium, and having a dimension of approximately 3.0 to about 4.0 millimeters when measured at the mid-suture.
Dorsal edge:
*Shape.*—Full, lightly grooved, and having a reasonably smooth margin.
Stone color: The color of the dry stone is generally considered a reddish brown, (approximately Greyed-Red Group RHS 178 B).
Tendency to split: Splitting has rarely been noted.
Kernel:
*Size.*—The kernel is considered medium-large.
*Form.*—Considered ovoid.
*Pellicle.*—Pubescent.
*Color.*—(RHS Greyed-Orange Group N167 A).
Use: The subject variety 'Burnectseventeen' is considered to be a nectarine tree of the late season of maturity, and which produces fruit that are considered firm, attractively colored, and which are useful for both local and long distance shipping.
Keeping quality: Excellent. Fruit has stored well up to 25 days after harvest at 1.0 degree Celsius.
Shipping quality: Considered good. The fruit of the new nectarine variety showed minimal bruising of the flesh or skin damage after being subjected to normal harvesting and packing procedures.
Resistance to insects and disease: No particular susceptibilities were noted. The present variety has not been tested to expose or detect any susceptibilities or resistances to any known plant and/or fruit diseases.

Although the new variety of nectarine tree possesses the described characteristics when grown under the ecological conditions prevailing near Fowler, Calif., in the central part of the San Joaquin Valley of California, it should be understood that variations of the usual magnitude and characteristics incident to changes in growing conditions, fertilization, pruning, pest control and horticultural management are to be expected.

Having thus described and illustrated our new variety nectarine tree, what we claim is new and desired to secure by Plant Letters Patent is:

1. A new distinct variety of nectarine tree substantially as illustrated and described, and which is characterized principally as to novelty by producing an attractively colored yellow-fleshed, clingstone nectarine which is mature for harvesting approximately August 7 to August 12 under the ecological conditions prevailing in the San Joaquin Valley of central California.

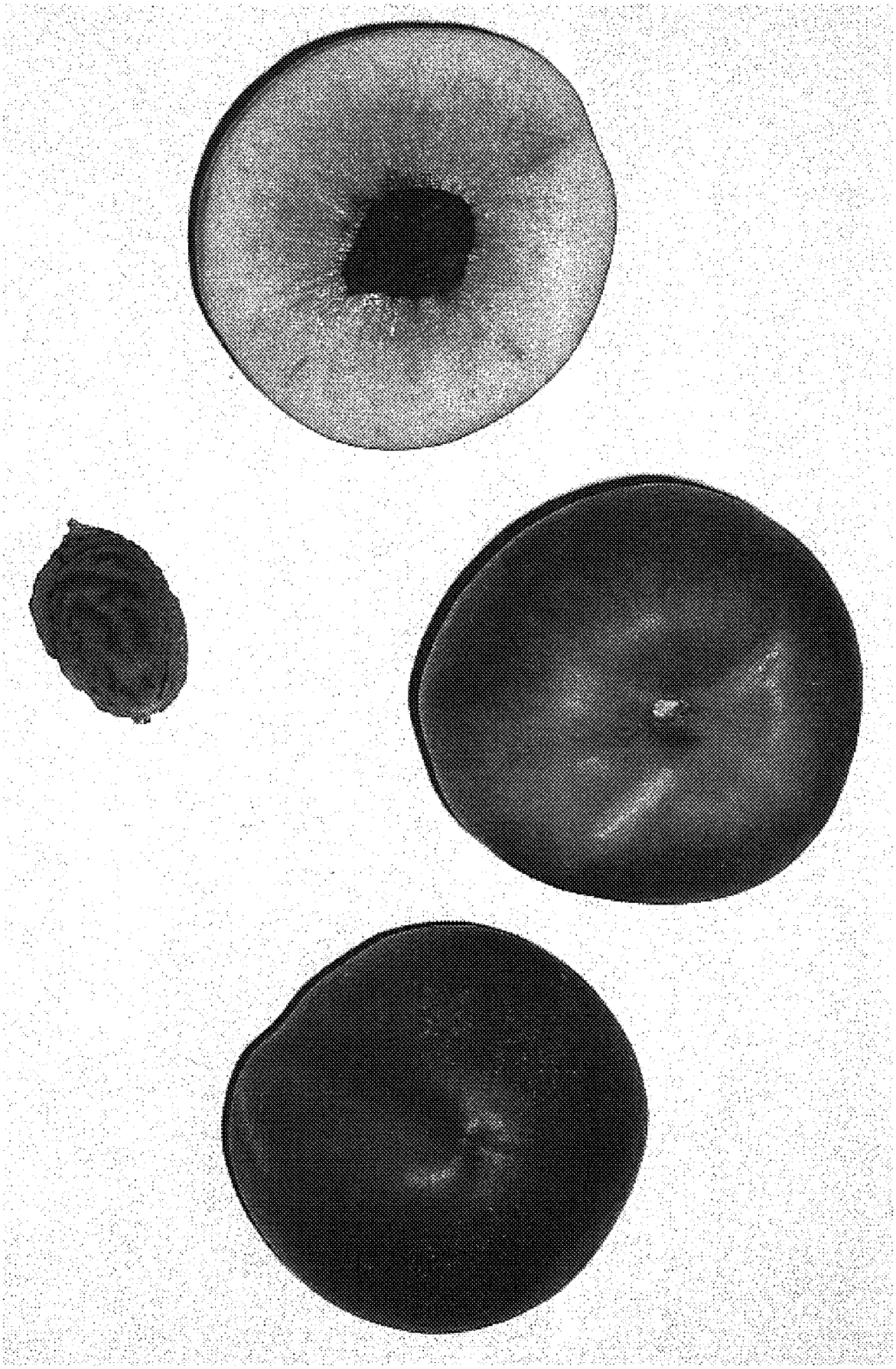

* * * * *